US012025628B2

(12) United States Patent
Huang et al.

(10) Patent No.: US 12,025,628 B2
(45) Date of Patent: Jul. 2, 2024

(54) TEST STRIP CODE READER AND ANALYTE DETECTION DEVICE

(71) Applicant: Bionime Corporation, Taichung (TW)

(72) Inventors: Li-Kang Huang, Taichung (TW); Chun-Mu Huang, Taichung (TW)

(73) Assignee: BIONIME CORPORATION, Taichung (TW)

( * ) Notice: Subject to any disclaimer, the term of this patent is extended or adjusted under 35 U.S.C. 154(b) by 340 days.

(21) Appl. No.: 17/499,547

(22) Filed: Oct. 12, 2021

(65) Prior Publication Data

US 2022/0113324 A1 Apr. 14, 2022

Related U.S. Application Data

(60) Provisional application No. 63/090,814, filed on Oct. 13, 2020.

(51) Int. Cl.
*G01N 1/00* (2006.01)
*G01N 33/66* (2006.01)
*G01N 35/00* (2006.01)

(52) U.S. Cl.
CPC ....... *G01N 35/00732* (2013.01); *G01N 33/66* (2013.01); *G01N 35/00029* (2013.01); *G01N 2035/00039* (2013.01); *G01N 2035/00108* (2013.01); *G01N 2035/00752* (2013.01); *G01N 2800/042* (2013.01)

(58) Field of Classification Search
None
See application file for complete search history.

(56) References Cited

U.S. PATENT DOCUMENTS 10,718,752 B2 * 7/2020 Chen ...................... G01N 27/04

* cited by examiner

*Primary Examiner* — Jyoti Nagpaul
(74) *Attorney, Agent, or Firm* — Volpe Koenig III

(57) ABSTRACT

A test strip code reader is provided. The test strip code reader includes a test strip carrier for accommodating a test strip, a first conductive element for decoding a code of the test strip, a second conductive element configured to be in a contact state or a separation state with the first conductive element, and an activation element having a body and a plurality of protrusions, wherein the body is used to prevent the first conductive element from being contaminated, and according to whether the plurality of protrusions are actuated by the test strip, the contact state or the separation state between the first conductive element and the second conductive element is determined to decode the code of the test strip.

17 Claims, 9 Drawing Sheets

TEST STRIP CODE READER AND ANALYTE DETECTION DEVICE

CROSS-REFERENCE TO RELATED APPLICATION AND CLAIM OF PRIORITY

This application claims the benefit of U.S. Provisional Application No. 63/090,814, filed on Oct. 13, 2021, in the United States Patent and Trademark Office, the disclosures of which are incorporated herein in their entirety by reference.

FIELD OF THE INVENTION

The present invention is related to a test strip code reader for applying to an analyte detection device. Particularly, the present invention is related to a test strip code reader having activation element which is integrally formed, and the test strip code reader is capable of reading codes.

BACKGROUND OF THE INVENTION

A device is used to measure physiological parameters (such as blood glucose, cholesterol, uric acid, blood ketone concentration and pH). A physiological sample is placed on a test strip to perform measurement under preset device conditions. Some test strip code reader can perform different types of measurements according to the physiological samples on the test strips with different codes of each test strip or determine the calibration factor corresponding to the test strip.

In order to allow the test strip code reader to confirm different types of measurements, or to achieve anti-counterfeiting effect, a coding area can be formed on a certain part of the lower surface of the test strip. The code area is a coding layout including a plurality of coding elements, wherein each of the coding elements has a coding factor, and a specific code is formed according to the combination of different coding factors to determine the measurement type of the test strip or the calibration factor corresponding to the test strip. For example, the coding area of the lower surface of the test strip has a coding layout formed by a plurality of holes, and the combination of each deep or shallow hole determines different coding factors. Therefore, the analyte measurement module determines the specific measurement type for the sample on the test strip or the calibration factor corresponding to the test strip according to the specific code formed by the combination of various coding factors.

Specifically, before the test strip code reader measures the samples in the test strip, the test strip code reader first reads the specific code formed by these holes for decoding, so as to identify the type of the test strip, so that the test strip sample reader selects the appropriate measurement configuration, and can also have the function of anti-counterfeiting at the same time.

In the test strip code reader of the prior art, an array of conductive elastic pieces including conductive parts and elastic extension elements are arranged in operating slots of the test strip code reader, and is used to abut against an activation element above it via a blocking element, so that the activation element can be closely attached to the inner surface of each hole in the coding area on the lower surface of the test strip. When there are protrusions on the inner surface of the hole, the activation element is pressed down, so that the conductive part is separated from the ground element, causing a circuit formed by the array of conductive elastic pieces and a conductive area on the circuit board to be disconnected; when there are no protrusions on the inner surface of the hole, the activation element will not be pressed down, and the conductive part remains in contact with the ground element, so that the aforementioned circuit remains conductive. Therefore, according to whether there are protrusions on the inner surface of the hole to press the activation element down or not to press the activation element down, the circuit between the array of conductive elastic pieces and a ground point is determined whether it is connected, and the code formed by the inner surface of the plurality of holes on the lower surface of the test strip is confirmed.

However, for example, in the test strip code reader disclosed in U.S. Pat. No. 10,718,752B2, each element is an independent and separate element, which is arranged in each operation slot. Although a blocking element is provided, the sample still has the risk of entering the analyte measurement module from the gap between the operation slot and its components, since each blocking element is only used for each operation slot for the pollution protection, which leads to an increased chance of pollution.

Furthermore, the activation element and the blocking element in the aforementioned known test strip code reader are also independent and separate components, and the same amount of activation elements and blocking elements as the amount of the holes on the test strip should be configured in the code reader, which also causes the burden of preparing materials. In addition, the activation element and the blocking element are also small elements, which also leads to many and complicated and time-consuming assembly operations.

It is therefore the Applicant's attempt to deal with the above situations encountered in the prior art.

SUMMARY OF THE INVENTION

In order to overcome the problems of the known test strip code reading device, where, in particular, the accuracy of interpretation and the effect of improving the convenience of assembly should both exist, the present invention provides a test strip code reader, including: a test strip carrier for accommodating a test strip, wherein the test strip has a plurality of code corresponding areas; a base body configured under the test strip carrier, and having a plurality of operation holes; a positioning part configured under the base body, and having a plurality of operation slots corresponding to the plurality of operation holes; a first conductive element configured between the base body and the plurality of operation slots, wherein the first conductive element is used as a shared end of a plurality of coding signals; a plurality of second conductive elements respectively accommodated in each of the operation slots, and the plurality of second conductive elements are configured to be in a contact state or a separation state with the first conductive element; an activation element configured between the base body and the first conductive element, and having a body and a plurality of protrusions, wherein the plurality of protrusions respectively pass through the plurality of operation holes to respectively correspond to the code corresponding areas of the test strip; and a circuit board configured at a bottom of the base body, wherein a coding signal reflects the contact state or the separation state between each of the second conductive elements and the first conductive element according to whether the protrusions are actuated by the test strip or not.

In accordance with another aspect of the present disclosure, an analyte detection system for receiving a test strip to perform an analyte detection is disclosed. The analyte detection system includes: a test strip code reader, including: a test strip carrier receiving the test strip; a first conductive element used as a shared end of a plurality of coding signals; a plurality of second conductive elements configured to be in a contact state or a separation state with the first conductive element; and an activation element having a body and a plurality of protrusions, wherein the body prevents the first conductive element from being contaminated, and according to whether the plurality of protrusions are actuated by the test strip, the contact state or the separation state between the first conductive element and each of the second conductive elements decodes the code of the test strip; an upper cover configured above the test strip code reader, and at least partially covering a top surface of the test strip code reader; and a lower cover configured under the test strip code reader to cover a bottom surface of the test strip code reader.

In accordance with one more aspect of the present disclosure, an analyte detection device for detecting a biological sample through a test strip is disclosed, wherein the test strip has a coding layout, and the coding layout has a plurality of coding elements. The analyte detection device includes: a device body; a plurality of upper operation pieces configured in the device body, and respectively corresponding to the plurality of coding elements; a plurality of lower operation pieces configured in the device body, and respectively corresponding to the plurality of upper operation pieces, wherein the coding layout is made through a cooperation of the plurality of upper operation pieces and the plurality of lower operation pieces; and an antipollution element configured in the device body and located between the plurality of upper operation pieces and the plurality of lower operation pieces, and the antipollution elements and the plurality of upper operation pieces are integrally formed to form a one-piece element, wherein the one-piece element has a periphery, and even if the biological sample has an overflow situation in the analyte detection device, the periphery isolates the biological sample from a possible influence on a detection of the biological sample.

BRIEF DESCRIPTION OF THE DRAWINGS

Other objectives, advantages and efficacies of the present invention will be described in detail below taken from the preferred embodiments with reference to the accompanying drawings.

DETAILED DESCRIPTION OF THE PREFERRED EMBODIMENTS

Figure 1:
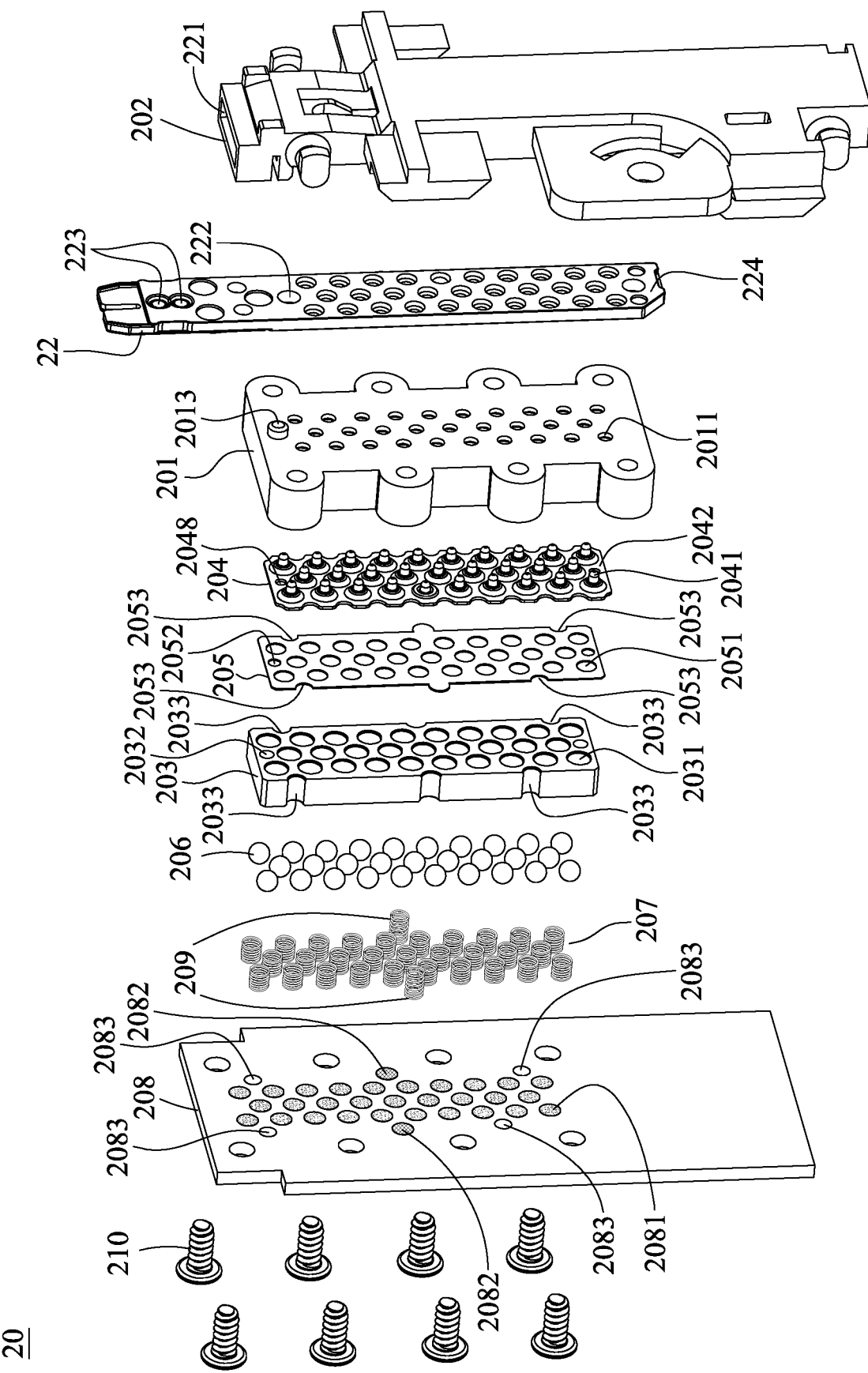
FIG. 1 shows a schematic diagram of the structure of the test strip code reader of the present invention.

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed. In the preferred embodiments, the same reference numeral represents the same element in each embodiment.

In order to improve the problems of the known technology, the present invention provides the following embodiments.

Figure 6A:
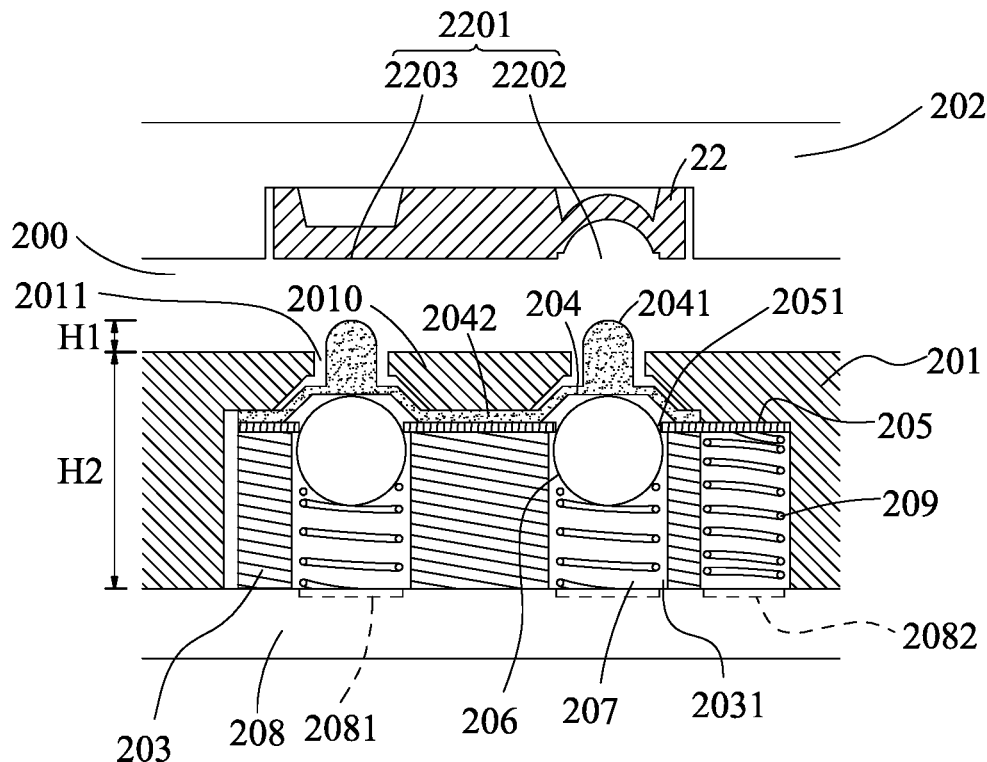
FIG. 6A shows a partial sectional diagram of the test strip code reader of the present invention when the test strip is not pressed down.
Figure 6B:
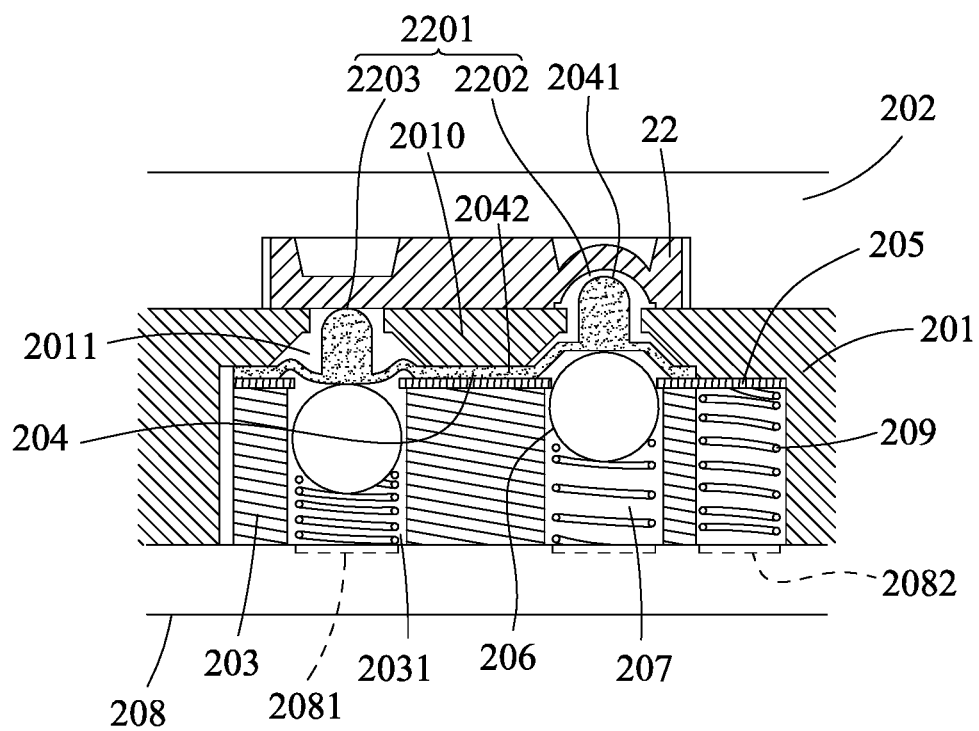
FIG. 6B shows a partial sectional diagram of the test strip code reader of the present invention when the test strip is pressed down.

Please refer to FIG. 1, which a schematic diagram of the structure of the test strip code reader of the present invention. The test strip code reader 20 of the present invention includes a test strip carrier 202, a base body 201, an activation element 204, a first conductive element 205, a positioning part 203, a second conductive element 206, a second conductive elastic element 207, a first conductive elastic element 209 and a circuit board 208, wherein the elements above are locked and fixed using screws 210 after assembly. The test strip 22 will be inserted into the test strip code reader 20 to read the test strip code. The test strip 22 has a positioning hole 222 and an electrode, wherein the electrode includes an electrode action surface (not shown) and a signal output end 223, and an electrode material of the electrode preferably is gold, for example, the materials using in Rightest® Blood test strip and cooperating with the embedded gold electrode test strip technology (Validus®Technology), so that the current generated by the test strip has better stability and conductivity. The test strip 22 has an upper surface 224 and a lower surface (not shown), wherein the lower surface of the test strip 22 has a plurality of code corresponding areas 2201, and each of the code corresponding areas 2201 is a code element, which is presented as a plane 2203 or an concave groove (as shown in FIGS. 6A and 6B). The combination of the plurality of plane 2203 or concave groove 2202 of the lower surface of the test strip 22 forms a coding area, to determine a coding layout of the test strip 22. In another embodiment, the code corresponding area 2201 is not limited to the plane or the convex groove, and may also be in other corresponding forms. In another embodiment, the plurality of code corresponding areas 2201 can be configured on the upper surface 224 of the test strip 22. The test strip code reader 20 of the present invention can detect type of analytes (such as blood glucose, cholesterol, uric acid, blood ketone concentration and pH) in the biological sample (such as blood) or to determine the calibration factor corresponding to the test strip 22 via the test strip 22.

Figure 2:
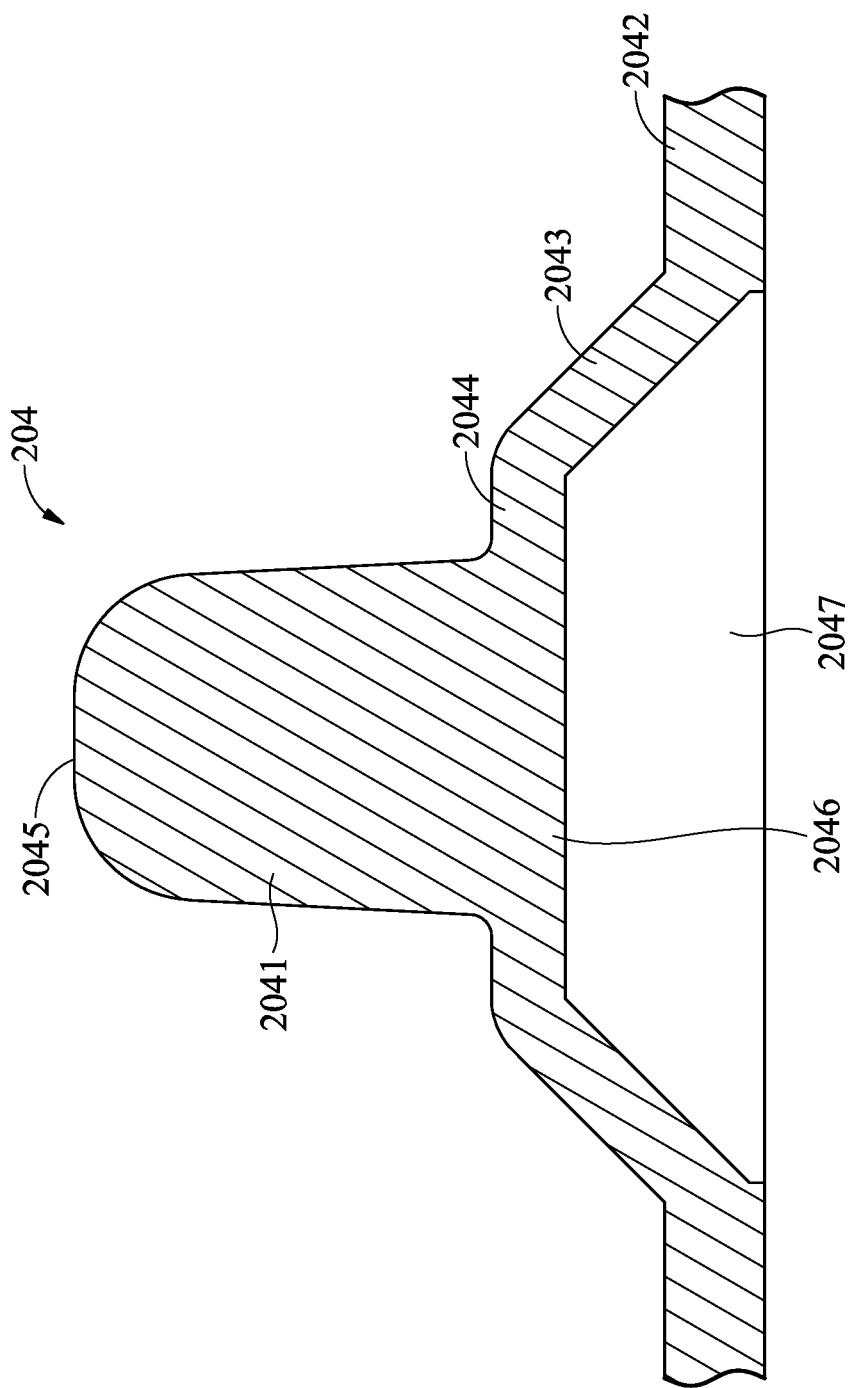
FIG. 2 shows a partial sectional diagram of the activation element of the test strip code reader of the present invention.

Please refer to FIG. 2, which is a partial sectional diagram of the activation element of the test strip code reader of the present invention. The activation element 204 of the present invention is an integrally formed array of protrusive elastic sheet, which is configured between the base body 201 and the first conductive element 205. The activation element 204 can be cooperated with the test strip 22 to perform a decoding operation, and can also prevent dirt and pollutants from entering an operation slot 2031 of the positioning part 203. The activation element 204 includes a body 2042 and a plurality of protrusions 2041, wherein each of the protrusions 2041 has an upper end 2045 and a lower end 2046, and the positions of the upper ends 2045 corresponds to each of the code corresponding area 2201. An elastic ring 2043 and a lateral annulus 2044 are configured between the lower end 2046 and the surface of the body 2042, wherein the elastic ring 2043 is connected to the body 2042 and the lateral annulus 2044, and the lateral annulus 2044 is connected to the elastic ring 2043 and the lower ends 2046 of each of the protrusions 2041. The elastic ring 2043 has a slant angle, so that there is a gap 2047 below each of the protrusions 2041, and the lower end 2046 of the protrusions 2041 provides a repeated bounce up and press down via the gap 2047. The thickness of the elastic ring 2043 can be controlled to 0.05-0.3 mm, preferably 0.07-0.2 mm, and more preferably 0.09-0.15 mm, so that because of the thickness of the elastic ring 2043, the activation element 204 ensures more than 1 million times, even more than 10 million times, of repeated pressing, and can still maintain the resilience and the life level of no breakage. Therefore, through the application of this kind of activation element in this field, it also provides a life level and reliability that the industry cannot match. In addition, each of the protrusions 2041 can be individually stressed, will not be affected by the neighboring protrusions 2041, and will not cause the wrong test strip code to be read. The elastic ring 2043 and the lateral annulus 2044 around the protrusions 2041 can decrease the force required for pressing down the elastic ring 2043. The upper end 2045 of each of the protrusions 2041 has a flat surface of 0.2 mm-0.5 mm, preferably 0.3 mm-0.5 mm, which causes the plane of the test strip 22 to be effectively contacted to prevent the protrusions 2041 from tilting and falling when the plane of the test strip 22 is pressed down, so as to assist the test strip code reader 20 to perform effectively.

The activation element 204 of the present invention is not only used for decoding and activation, but also used for anti-polluting and/or dust-proofing. The activation element 204 of the present invention can miniaturize the overall volume, simplify the number of parts and thin the thickness to simplify the assembly process of the test strip code reader 20. The plurality of the protrusions 2041, the lateral annulus 2044, the elastic ring 2043 and the body 2042 of the activation element 204 are integrally formed. The material of the activation element 204 should have elasticity, and the material can be composed of rubber, silicone or thermoplastic elastomers, such as thermoplastic rubber (TPR), thermoplastic vulcanizate (TPV), thermoplastic polyurethane (TPU), thermoplastic polyolefin (TPO) or thermoplastic polyether elastomer (TPEE), preferably silicone.

The material of the activation element 204 can be a material of Shore A hardness between 60-80 degrees, preferably the material of 70 degrees, which causes each protrusion 2041 not easy to deform when pressed, and control the thickness of the elastic ring 2043 between 0.05-0.3 mm, preferably between 0.07-0.2 mm, and more preferably between 0.09-0.15 mm. The elastic ring 2043 and the lateral annulus 2044 around the protrusions 2041 can decrease the force required for pressing down the elastic ring 2043, which causes the protrusions 2041 has a suitable elasticity/hardness coefficient to be used as the activation element 204, so as to correspond the plane 2203 or the concave groove 2202 of the test strip 22 to activate decoding.

Figure 3A:
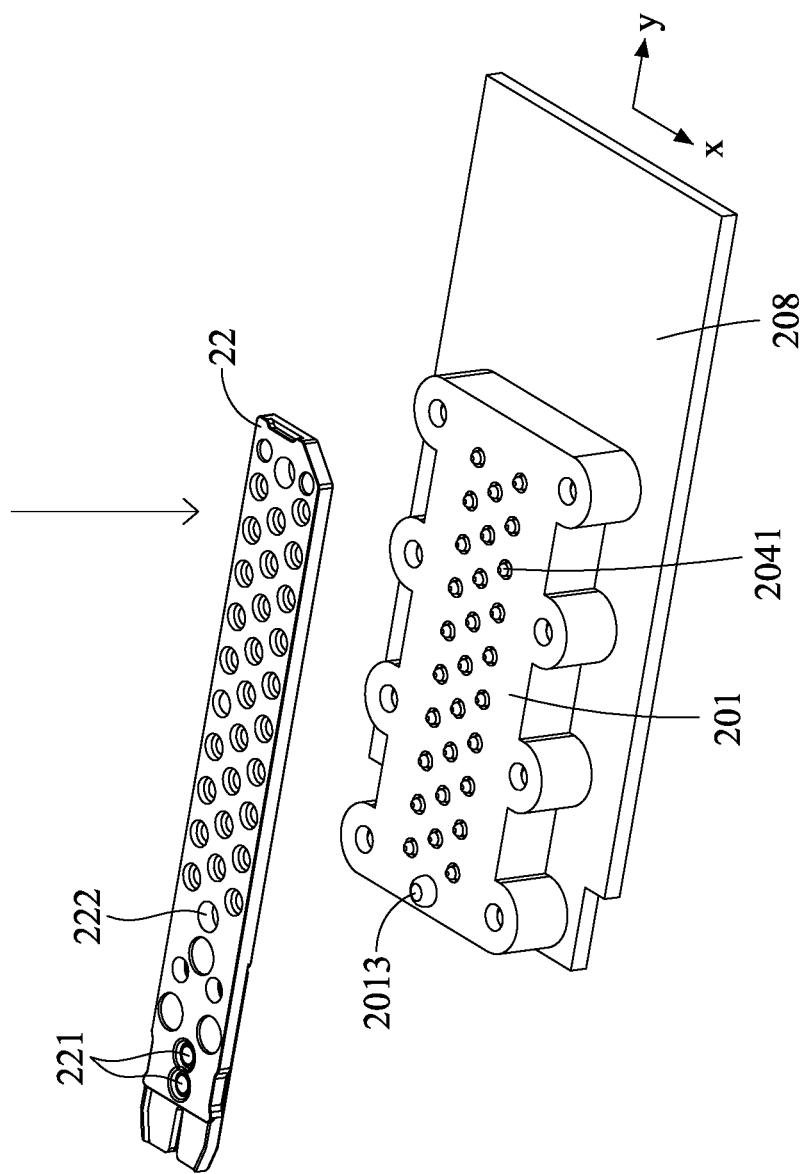
FIG. 3A shows a partial schematic diagram of the insertion of the test strip in the test strip code reader of the present invention.
Figure 3B:
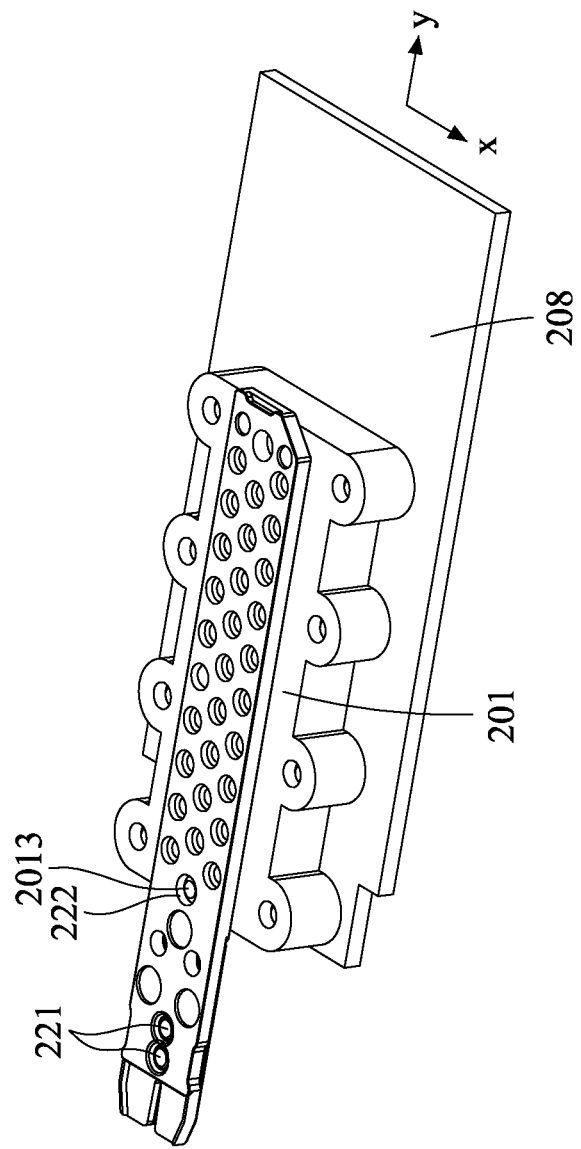
FIG. 3B shows a partial schematic diagram of the pressing of the test strip down to the test strip code reader of the present invention.

Please refer to FIGS. 1, 3A and 3B. The test strip carrier 202 of the test strip code reader 20 has a test strip insertion slot 221 for accommodating the test strip 22. The test strip carrier 202 connects a test strip import and export device (not shown). The base body 201 has a plurality of operation holes 2011. FIG. 3A shows the partial schematic diagram of the insertion of the test strip 22 in the test strip code reader 20. After the combination of the activation element 204 and base body 201, the upper end 2045 of the plurality of protrusions 2041 of the activation element 204 pass through the plurality of operation holes 2011 of the base body 201 and expose. When the test strip 22 is going to be read, the test strip 22 is inserted into the test strip insertion slot 221 in Y direction, guided to a scheduled position of the test strip insertion slot 221 by the test strip import and export device, and pressed down in the arrow direction. A first positioning column 2013 of the base body 201 corresponds to a positioning hole 222 of the test strip 22 for positioning, so that the coding area of the test strip 22 can correctly contact the activation element 204 (as shown in GIF. 3B). The first positioning column 2013 of base body 201 and the positioning hole 222 of the test strip 22 provide a positioning mechanism of the test strip 22 to avoid inserting the wrong test strip or the wrong way of inserting the test strip to improve measurement efficiency. The test strip import and export device can control the test strip 22 to automatically insert or eject the test strip insertion slot 221 to avoid squeeze and friction between the abnormal test strip 22 and the entrance of the test strip insertion slot 221 by accident, when the test strip 22 is manually inserted or ejected the test strip insertion slot 221. The test strip 22 is pressed down after entering the test strip carrier 202, which causes the plurality of protrusions 2041 of the activation element 204 have almost no friction and lateral contact interference, so that the height of the of the plurality of protrusions 2041 will not be decreased by abrasion. In another embodiment, the test strip code reader 20 does not need to be configured with the test strip import and export device, and the test strip 20 can be manually inserted into the test strip insertion slot 221 by the user to read the code.

Figure 4:
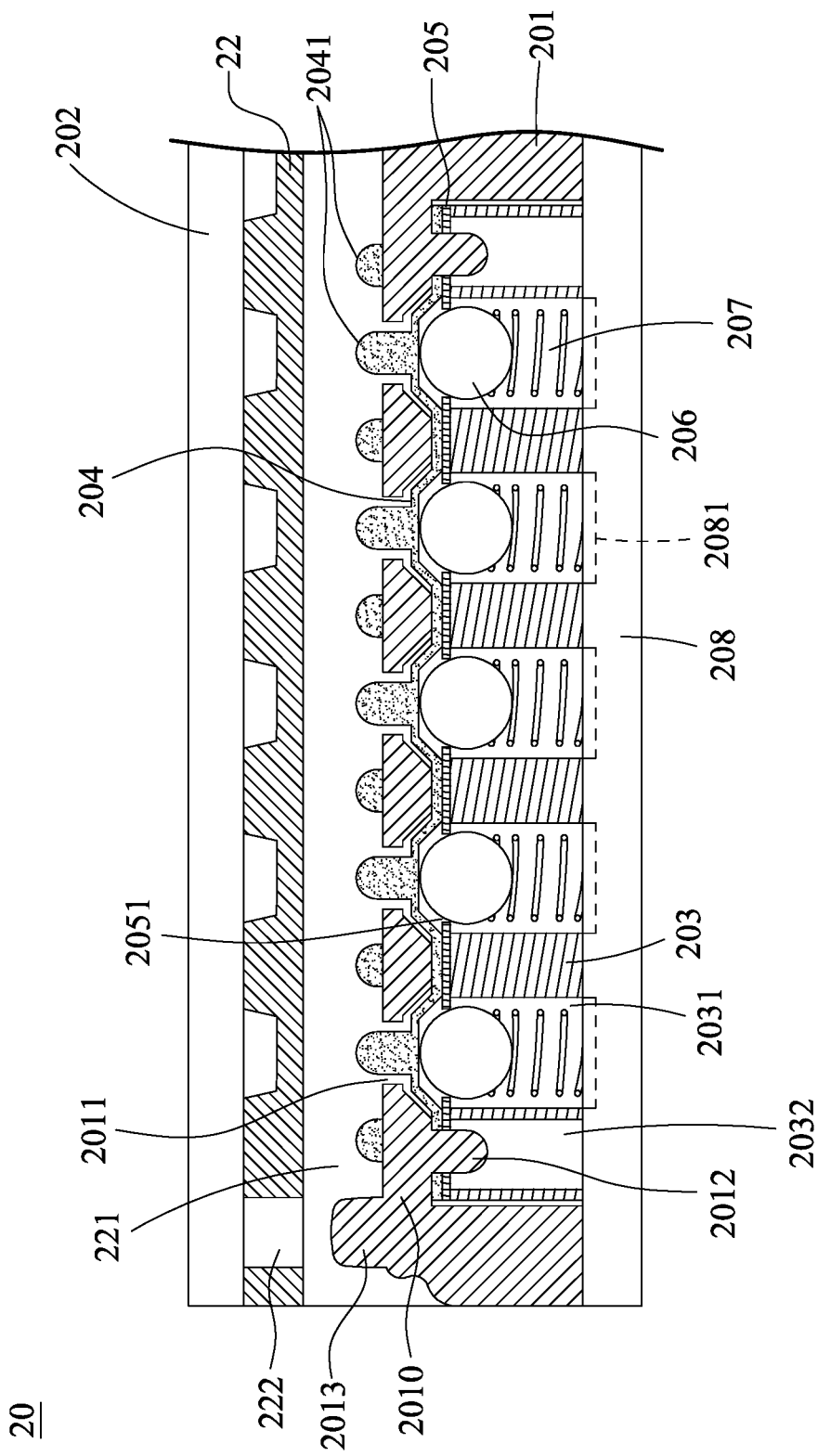
FIG. 4 shows a schematic sectional diagram of the relative position of the test strip and the test strip code reader of the present invention.
Figure 5A:
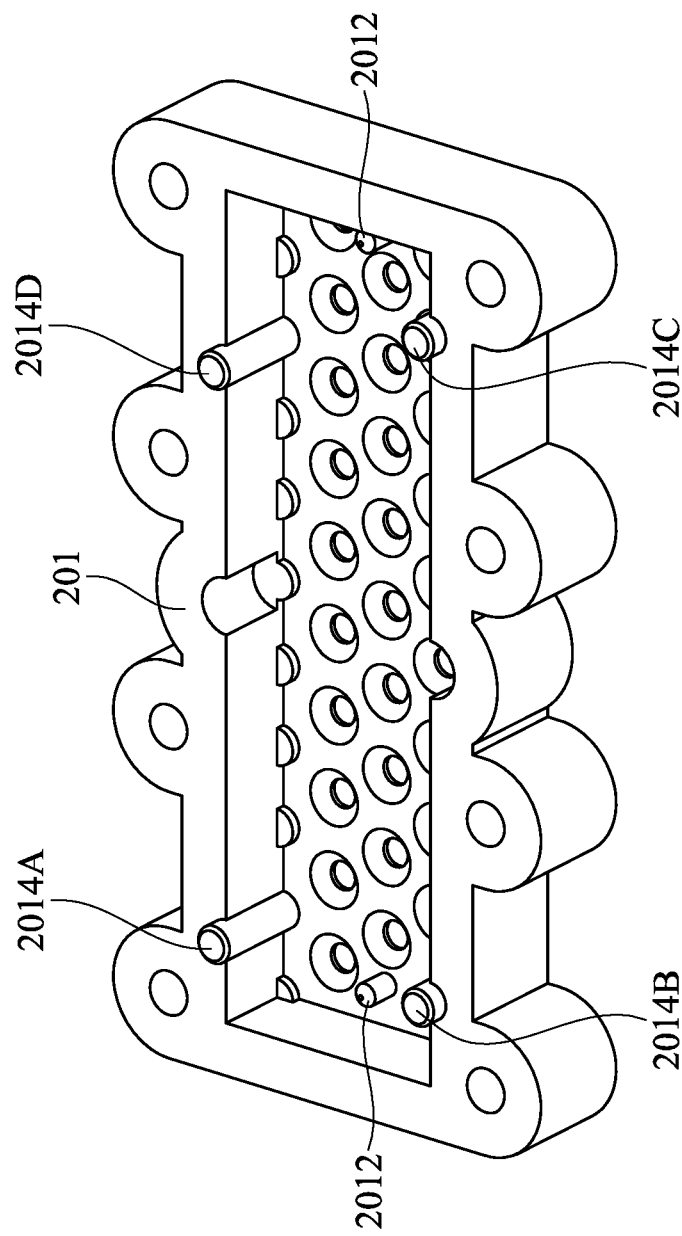
FIG. 5A shows a bottom perspective schematic diagram of the base body of the test strip code reader of the present invention.

Please refer to FIGS. 1, 4 and 5A, wherein FIG. 4 is the schematic sectional diagram of the relative position of the test strip and the test strip code reader, and FIG. 4 shows the sectional diagram of the test strip code reader in the Y direction. The base body 201 is configured below the test strip carrier 202. The base body 201 has a plurality of second positioning columns 2012, the positioning part 203 further includes a plurality of positioning slots 2032, and each of the second positioning columns 2012 is inserted in each of the positioning slots 2032 to fix the position between the base body 201 and the positioning part 203. In addition, each of the second positioning columns is passed through a plurality of positioning through holes 2048 of the activation element 204 and a plurality of positioning through holes 2052 of the first conductive element 205, to fix the position among the base body 201, the activation element 204, the first conductive element 205 and the positioning part 203.

Please refer to FIGS. 1, 4 and 6A-6B. The positioning part 203 has a plurality of operation slots. The base body 201 has a base body top layer 2010 covering on the activation element 204, wherein positions of the plurality of operation holes of the base body 201 respectively correspond to the positions of the plurality of code corresponding areas of the test strip 22, the activation element 204 is covered on first conductive element 205, and the upper ends 2045 of each of the protrusions 2041 of the activation element 204 respectively correspond to the plane 2203 or the concave groove 2202 of the plurality of code corresponding areas 2201 of the test strip 22. The upper ends 2045 of each of the protrusions 2041 are passed through each of the positioning holes 2011 formed in the base body top layer 2010. The lower ends 2046 of the plurality of protrusions 2041 abuts against the second conductive elements 206 in a plurality of operation slots 2031 formed in the positioning part 203. The plurality of operation slots 2031 of the positioning part 203 respectively correspond to the plurality of positioning holes 2011 of the base body top layer 2010. The first conductive element 205 has a through hole 2051 corresponding to the operation slot 2031, and a part of the second conductive element 206 is passed through the through hole 2051 to abut against the lower end 2046 of the protrusions 2041. The bottom of the second conductive element 206 is connected to the second conductive elastic element 207, and the bottom of the second conductive elastic element 207 is electrically connected to each of the second conductive areas of the circuit board 208. The circuit board 208 is configured at the bottom of the base body 201. The material of the positioning part 203 can be a plastic material, the first conductive element 205 is used as a ground element, the configuration of the second conductive element 206 is a spheroid or a column, and the circuit board 208 can be a printed circuit board (PCB), but not limited to this. In the present invention, the plurality of protrusions 2041 of the activation element 204 are used as a plurality of upper operation pieces, a part of the body 2042 connected around the plurality of protrusions 2041 of the activation element 204 is an antipollution element, and thus, the antipollution element and the plurality of upper operation pieces are integrally formed to form a one-piece element. The assembly of the first conductive element 205, the plurality of second conductive element 206 and the plurality of second conductive elastic element 207 are a plurality of lower operation pieces.

The first conductive element 205 of the present invention is a one-piece conductive element, so that the plurality of second conductive elements 206 share one first conductive element 205 to decode the code of the test strip 22. In addition, the diameter of the plurality of second conductive elements 206 is greater than the diameter of the plurality of through holes 2051 of the first conductive element 205, so that the plurality of second conductive elements 206 can pass through the plurality of through holes 2051 of the first conductive element 205 until the plurality of second conductive elements 206 contact with the first conductive element 205. Therefore, in the loop of the coding signal, the first conductive element 205 is used as a shared end of a plurality coding signals.

Figure 5B:
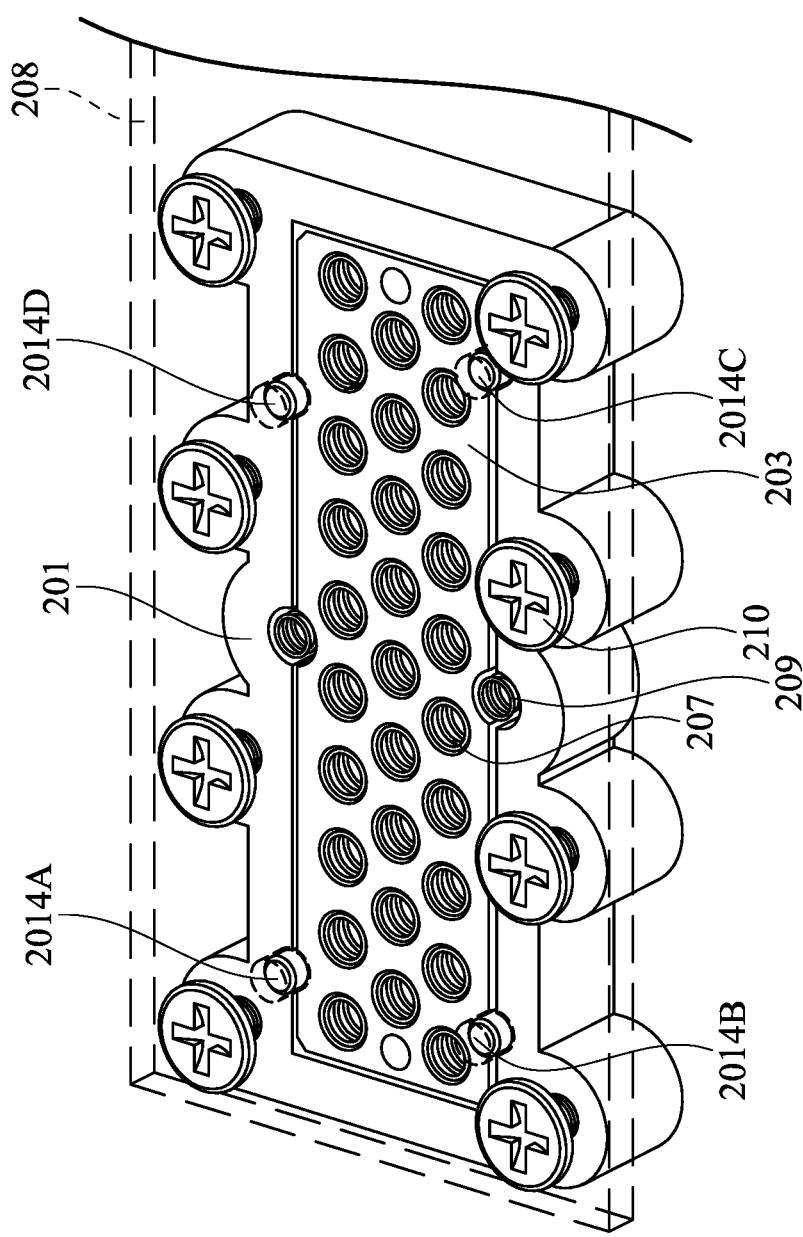
FIG. 5B shows a bottom perspective schematic diagram of the test strip code reader of the present invention.

Please refer to FIGS. 1, 5A and 5B. The base body 201 further includes a plurality of third positioning columns. In an embodiment in FIG. 5A of the present invention, there are four third positioning columns 2014A-2014D, wherein the position of one of the third positioning column 2014D is misaligned with the positions of the other three third positioning columns 2014A-2014C. Specifically, the four third positioning columns 2014A-2014D is arranged in an asymmetric configuration. The positioning part 203 further includes a plurality of positioning grooves 2033 corresponding to the positions of the plurality of third positioning columns 2014A-2014D, the first conductive element 205 further includes a plurality of positioning grooves 2053 corresponding to the positions of the plurality of third positioning columns 2014A-2014D, and the circuit board 208 includes a plurality of positioning through holes 2083 corresponding to the positions of the plurality of third positioning columns 2014A-2014D. The third positioning columns 2014A-2014D of the base body 201 can be passed through the plurality of positioning grooves 2033 of the positioning part 203, the plurality of positioning grooves 2053 of the first conductive element 205 and the plurality of positioning through holes 2083 of the circuit board 208, so that when the base body 201, the positioning part 203, the activation element 204, the first conductive element 205 and the circuit board 208 are assembled, the plurality of third positioning columns 2014A-2014D provide a foolproof assembly mechanism and a positioning reference (as shown in FIG. 5B).

Please refer to FIGS. 2, 6A and 6B, wherein FIGS. 6A and 6B respectively are partial sectional diagrams of the test strip code reader of the present invention when the test strip is not pressed down and pressed down. In FIG. 6A, when the test strip import and export device does not press the test strip 22 down, there is a void between the test strip carrier 202 and the base body 201, the protrusions 2041 of the activation element 204 do not contact the lower surface of the test strip 22. In FIG. 6B, when the test strip import and export device presses the test strip 22 down, the upper end 2045 of each of the protrusions 2041 of the activation element 204 is abutted against the planes 2203, or accommodated in the concave grooves 2202 at the lower surface of the test strip 22 above it. In FIGS. 6A and 6B, it can be seen that the first conductive element 205 is electrically connected to the first conductive elastic element 209, and the first conductive elastic element 209 is electrically connected to a first conductive area 2082.

When the lower surface of the test strip 22 corresponding to the upper end 2045 of the protrusion 2041 of the activation element 204 is the concave groove 2202, the upper end 2045 of the protrusion 2041 is accommodated in the concave groove 2202, and thus, the protrusions 2041 remains in the original height and position, and the second conductive element 206 is kept in contact with the corresponded first conductive element 205. Therefore, a loop formed by the first conductive area 2082 of the circuit board 208 through the first conductive elastic element 209, the first conductive element 205, the second conductive element 206 and the second conductive elastic element 207 to the second conductive area 208 of the circuit board 208 maintains a conductive state, which is decoded as a first coding signal.

When the lower surface of the test strip 22 corresponding to the upper end 2045 of the protrusion 2041 of the activation element 204 is the plane 2203, the upper end 2045 of the protrusion 2041 is abutted and pressed down by the plane 2203, and thus, the lower end 2046 of the protrusion 2041 presses the second conductive element 206 down below it, which causes the second conductive element 206 to be separated from the corresponded first conductive element 205 and the second conductive elastic element 207 is compressed. Therefore, a loop formed by the first conductive area 2082 of the circuit board 208 through the first conductive elastic element 209, the first conductive element 205, the second conductive element 206 and the second conductive elastic element 207 to the second conductive area 208 of the circuit board 208 becomes a non-conductive state, which is decoded as a second coding signal.

Therefore, the coding signal reflects the contact state or the separation state between the second conductive element and the first conductive element according to whether the protrusions are actuated by the test strip or not. Through the aforementioned code reading method in which the upper end 2045 of the protrusions 2041 of the activation element 204 is pressed against the lower surface of the test strip 22 with the plurality of planes 2203 or the plurality of concave grooves 2202, the test strip code reader 20 can read and decode the specific code formed by the combination of the plurality of planes 2203 or the plurality of concave grooves 2202 on the lower surface of the test strip 22, so as to identify the encoded information carried by the test strip 22. The encoded information is, for example, detection test strop types and calibration factors.

In addition to the activation element 204 against the lower surface of the test strip 22 above it to identify the code information of the test strip 22, since the activation element 204 is completely covered above the first conductive element 205, it can completely prevent the pollutants from entering the operation slots 2031 under the base body top layer 20010 of the test strip code reader 20. The surfaces of the first conductive element 205, the second conductive element 206, the first conductive elastic element 209 and the second conductive elastic element 207 of the test strip code reader 20 of the present invention can be electroplated with gold (Au) to decrease contact impedance, so as to effectively improve the contact conducting accuracy and significantly improve the service life After each of the protrusions 2041 of the activation element 204 being pressed down by the plane 2203 of the test strip 22, the height H1 of the pressed protrusions 2041 protruded the base body 201 preferably is 0.25 mm-0 mm (the height H1 in the embodiment of FIG. 6B of the present invention is 0 mm), and the force required for the plane 2203 of the test strip 22 to press each of the protrusions 2041 and the second conductive element 206 down to reach the height H1 is 9.9 g-15.1 g, so as to separate the second conductive element 206 and the corresponded first conductive element 205. The force required for each of the protrusions 2041 is independently pressed down to reach the height H1 is 2.4 g-4.5 g, so as to assist the code reading mechanism to perform effectively. The thickness of the base body 201 only needs 2.0-3.5 mm, and therefore, comparing with the known code reading device, the overall thickness of the test strip code reader 20 of the present invention is lighter and thinner.

Please refer to FIGS. 1, 2, 4 and 7. The present invention provides an analyte detection device 30, including a device body 310 and the test strip code reader 20 configured in the device body 310. The analyte detection device 30 can determine the coding layout of the test strip 22 through the cooperation of the plurality of upper operation pieces and the plurality of lower operation pieces. The one-piece insulating element of the test strip code reader 20 has a periphery for preventing the biological sample from overflowing. Even if the biological sample has the overflow situation in the test strip code reader 20, the periphery isolates the biological sample from a possible influence on the analyte detection.

Figure 7:
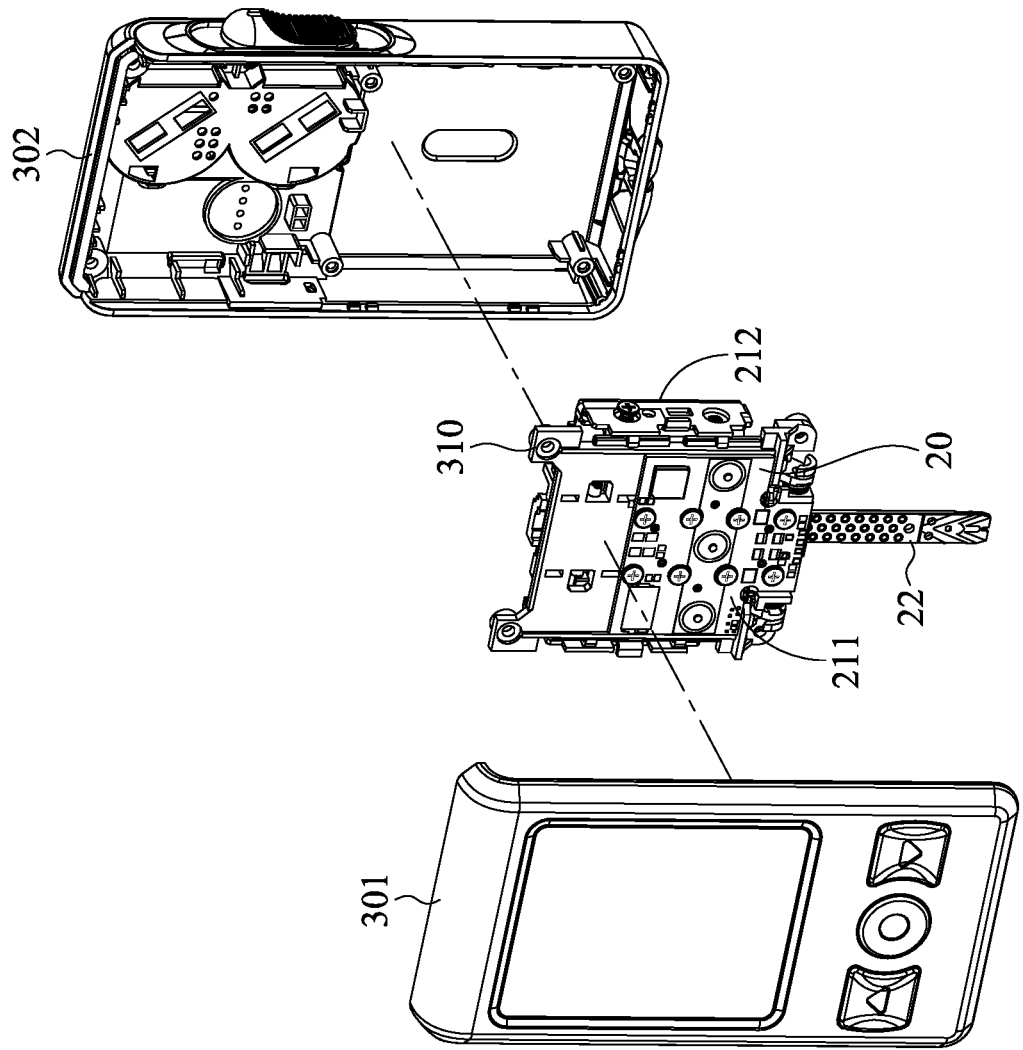
FIG. 7 shows a schematic diagram of the structure of the analyte detection device of the present invention.

Please refer to FIG. 7, which is a schematic diagram of the test strip code reader 20 to be assembled to the analyte detection device 30 of the present invention. The analyte detection device 30 includes the test strip code reader 20, an upper cover 301 and a lower cover 302. The test strip code reader 20 has a complete test strip code reading function. The test strip code reader 20 is connected to a power source (not shown), and has a top surface 211 and a bottom surface 212. When the upper cover 301, the lower cover 302 and the test strip code reader 20 of the analyte detection device 30 are assembled, the upper cover 301 is configured above the test strip code reader 20 and selectively covering the top surface 211 of the test strip code reader 20 completely or partially (the completely covering is shown in the embodiment of the present invention) for modifying the appearance of the front of the analyte detection device 30, and the lower cover 302 is configured under the test strip code reader 20 to cover the bottom surface 212 of the test strip code reader 20. The test strip code reader 20 is arranged in the upper cover 301 and the lower cover 302 of the analyte detection device 30, so that the analyte detection device 30 can have the functions provided by the test strip code reader 20. Therefore, the same test strip code reader 20 can be used to collocate with the upper cover and the lower cover with different appearances to facilitate manufacturers to produce different analyte detection devices. This mode can increase the process stability of the analyte detection device and speed up the product development time. In another embodiment, the upper cover 301 and the lower cover 302 can be integrally formed with the test strip code reader 20.

Please refer to FIGS. 6A and 6B. Compared with the prior art, it can be seen that the body 2042 and the plurality of protrusions 2041 of the activation element 204 of the present invention are integrally formed, and the activation element 204 is completely covered on the first conductive element 205 to provide both decoding and dust-proofing and anti-polluting functions. Therefore, the activation element 204 of the present invention can achieve the code reading function by pressing against the test strip as the function of the activation element in the known code reading device, and can complete the function of preventing the pollutant from entering the plurality of operation slots of the present invention as the blocking element in the known code reading device.

Therefore, the integrally formed activation element of the present invention can further replace the independent plurality of activation elements and blocking elements of the known code reading device. Because the amount of components is reduced, the space required for components in the test strip code reader is eliminated, and the thickness of the test strip code reader is reduced. The thickness of the base body 201 of the present invention can be as thin as 3.3 mm. In addition to solving the inventory problems caused by simplifying the assembly and reducing the amount and types of the components, because the activation element and the plurality of protrusions on the surface are integrally formed, there is no gap at the edge of each operation slot as the known code reading device. Therefore, the present invention can greatly and effectively prevent contaminants from entering the plurality of operation slots.

The thickness of the elastic ring 2043 of the activation element 204 of the present invention is controlled between 0.05-0.3 mm, preferably between 0.07-0.2 mm, and more preferably between 0.09-0.15 mm for further reducing the thickness of the test strip code reader 20. On the other hand, the elastic ring 2043 of the activation element 204 of the present invention can withstand at least 1 million times, even more than 10 million times, of repeated pressing without breakage, which can improve the reliability of the test strip code reader 20 of the present invention, and also can provide the life level and the reliability that the industry cannot match in the art.

Embodiments

1. A test strip code reader, including: a test strip carrier for accommodating a test strip, wherein the test strip has a plurality of code corresponding areas; a base body configured under the test strip carrier, and having a plurality of operation holes; a positioning part configured under the base body, and having a plurality of operation slots corresponding to the plurality of operation holes; a first conductive element configured between the base body and the plurality of operation slots, wherein the first conductive element is used as a shared end of a plurality of coding signals; a plurality of second conductive elements respectively accommodated in each of the operation slots, and each the of second conductive element is configured to be in a contact state or a separation state with the first conductive element; an activation element configured between the base body and the first conductive element, and having a body and a plurality of protrusions, wherein the plurality of protrusions respectively pass through the plurality of operation holes to respectively correspond to the code corresponding areas of the test strip; and a circuit board configured at a bottom of the base body, wherein a coding signal reflects the contact state or the separation state between each of the second conductive elements and the first conductive element according to whether the protrusions are actuated by the test strip or not.

2. The test strip code reader according to Embodiment 1, wherein each of the plurality of code corresponding areas of the test strip is one of a plane and a concave groove.

3. The test strip code reader according to Embodiment 1 or 2, wherein each of the protrusions has an upper end and a lower end, the lower end abuts the second conductive element, and when the test strip is pressed, the plane abuts the upper ends of the corresponding protrusions and the concave groove accommodates the corresponding protrusions.

4. The test strip code reader according to any one of Embodiments 1 to 3, wherein when the plane abuts the upper end of the corresponding protrusion to press the corresponding protrusion, the lower end of the corresponding protrusion presses the corresponding second conductive element, so as to separate the corresponding second conductive element from the first conductive element to form a non-conductive state to be decoded as a first coding signal, and when the concave groove accommodates the upper end of the corresponding protrusion, the corresponding second conductive element is kept in contact with the first conductive element to maintain a conductive state to be decoded as a second coding signal.

5. The test strip code reader according to any one of Embodiments 1 to 4, wherein the activation element is made of an elastic material, and the activation element further includes an elastic ring located between the lower end of each of the plurality of protrusions and the body of the activation element.

6. The test strip code reader according to any one of Embodiments 1 to 5, wherein the activation element further includes a lateral annulus located between the elastic ring and each of the plurality of protrusions.

7. The test strip code reader according to any one of Embodiments 1 to 6, wherein the elastic material has a Shore A hardness between 60-80 degrees.

8. The test strip code reader according to any one of Embodiments 1 to 7, wherein the body of the activation element totally covers on the first conductive element, to prevent a pollutant from entering the operation slots.

9. The test strip code reader according to any one of Embodiments 1 to 8, wherein the body of the activation element and the plurality of protrusions of the activation element are integrally formed.

10. The test strip code reader according to any one of Embodiments 1 to 9, further including a first conductive elastic element electrically connected to the first conductive element.

11. The test strip code reader according to any one of Embodiments 1 to 10, further including a second conductive elastic element connected to each of the plurality of second conductive elements, so that each of the plurality of second conductive elements is in contact with the first conductive element, and the second conductive elastic element is in contact with the plurality of conductive areas on the circuit board.

12. The test strip code reader according to any one of Embodiments 1 to 11, wherein the base body further includes a positioning column, the positioning part further includes a positioning slot, and the positioning column passes through a positioning through hole of the first conductive element and is inserted in the positioning slot to position the activation element, the first conductive element and the positioning part.

13. The test strip code reader according to any one of Embodiments 1 to 12, wherein the base body further includes a positioning column, and the test strip has a positioning hole for providing a positioning mechanism between the base body and the test strip.

14. The test strip code reader according to any one of Embodiments 1 to 13, wherein the base body further includes a plurality of positioning columns arranged in an asymmetric configuration.

15. The test strip code reader according to any one of Embodiments 1 to 14, wherein: the positioning part further includes a plurality of first positioning grooves, the first conductive element further includes a plurality of second positioning grooves and the circuit board further includes a plurality of positioning through holes; the plurality of first positioning grooves, the plurality of second positioning grooves and the plurality of positioning through holes are disposed corresponding to the plurality of positioning columns; and each of the plurality of positioning columns passes through respective ones of the corresponding plurality of first positioning grooves, the corresponding plurality of second positioning grooves and the corresponding plurality of positioning through holes to provide a foolproof assembly mechanism and a positioning reference.

16. An analyte detection system for receiving a test strip to perform an analyte detection, including: a test strip code reader, including: a test strip carrier receiving the test strip; a first conductive element used as a shared end of a plurality of coding signals; a plurality of second conductive elements configured to be in a contact state or a separation state with the first conductive element; and an activation element having a body and a plurality of protrusions, wherein the body prevents the first conductive element from being contaminated, and according to whether the plurality of protrusions are actuated by the test strip, the contact state or the separation state between the first conductive element and each of the second conductive element decodes the code of the test strip; an upper cover configured above the test strip code reader, and at least partially covering a top surface of the test strip code reader; and a lower cover configured under the test strip code reader to cover a bottom surface of the test strip code reader.

17. The analyte detection system according to Embodiment 16, wherein the test strip code reader further includes a circuit board having a conductive area, the conductive area electrically connects to each of the second conductive elements, and a coding signal is responsive to the contact state or the separation state of the first conductive element and the second conductive element.

18. The analyte detection system according to Embodiment 17 or 18, wherein the body and the plurality of protrusions are integrally formed.

19. An analyte detection device for detecting a biological sample through a test strip, wherein the test strip has a coding layout, the coding layout has a plurality of coding elements, and the analyte detection device includes: a device body; a plurality of upper operation pieces configured in the device body, and respectively corresponding to the plurality of coding elements; a plurality of lower operation pieces configured in the device body, and respectively corresponding to the plurality of upper operation pieces, wherein the coding layout is made through a cooperation of the plurality of upper operation pieces and the plurality of lower operation pieces; and an antipollution element configured in the device body and located between the plurality of upper operation pieces and the plurality of lower operation pieces, and the antipollution elements and the plurality of upper operation pieces are integrally formed to form a one-piece element, wherein the one-piece element has a periphery, and even if the biological sample has an overflow situation in the analyte detection device, the periphery isolates the biological sample from a possible influence on a detection of the biological sample.

Although the present invention has been described with reference to certain exemplary embodiments thereof, it can be understood by those skilled in the art that a variety of modifications and variations may be made to the present invention without departing from the spirit or scope of the present invention defined in the appended claims, and their equivalents.

What is claimed is:

1. A test strip code reader, comprising:
a test strip carrier for accommodating a test strip, wherein the test strip has a plurality of code corresponding areas;
a base body configured under the test strip carrier, and having a plurality of operation holes;
a positioning part configured under the base body, and having a plurality of operation slots corresponding to the plurality of operation holes;
a first conductive element configured between the base body and the plurality of operation slots, wherein the first conductive element is used as a shared end of a plurality of coding signals;
a plurality of second conductive elements respectively accommodated in each of the operation slots, and each of the second conductive element is configured to be in a contact state or a separation state with the first conductive element;
an activation element configured between the base body and the first conductive element, and having a body and a plurality of protrusions, wherein the body of the activation element and the plurality of protrusions of the activation element are integrally formed such that the body prevents the first conductive element from being contaminated and the plurality of protrusions respectively pass through the plurality of operation holes to respectively correspond to the code corresponding areas of the test strip; and
a circuit board configured at a bottom of the base body, wherein a coding signal reflects the contact state or the separation state between each of the second conductive elements and the first conductive element according to whether the protrusions are actuated by the test strip or not.

2. The test strip code reader as claimed in claim 1, wherein each of the plurality of code corresponding areas of the test strip is one of a plane and a concave groove.

3. The test strip code reader as claimed in claim 2, wherein each of the protrusions has an upper end and a lower end, the lower end abuts the second conductive element, and when the test strip is pressed, the plane abuts the upper ends of the corresponding protrusion and the concave groove accommodates the corresponding protrusion.

4. The test strip code reader as claimed in claim 3, wherein when the plane abuts the upper end of the corresponding protrusion to press the corresponding protrusion, the lower end of the corresponding protrusion presses the corresponding second conductive element, so as to separate the corresponding second conductive element from the first conductive element to form a non-conductive state to be decoded as a first coding signal, and when the concave groove accommodates the upper end of the corresponding protrusion, the corresponding second conductive element is kept in contact with the first conductive element to maintain a conductive state to be decoded as a second coding signal.

5. The test strip code reader as claimed in claim 3, wherein the activation element is made of an elastic material, and the activation element further includes an elastic ring located between the lower end of each of the plurality of protrusions and the body of the activation element.

6. The test strip code reader as claimed in claim 5, wherein the activation element further includes a lateral annulus located between the elastic ring and each of the plurality of protrusions.

7. The test strip code reader as claimed in claim 5, wherein the elastic material has a Shore A hardness between 60-80 degrees.

8. The test strip code reader as claimed in claim 1, wherein the body of the activation element totally covers on the first conductive element, to prevent a pollutant from entering the operation slots.

9. The test strip code reader as claimed in claim 1, further comprising a first conductive elastic element electrically connected to the first conductive element.

10. The test strip code reader as claimed in claim 9, further comprising a second conductive elastic element connected to each of the plurality of second conductive elements, so that each of the plurality of second conductive elements is in contact with the first conductive element, and the second conductive elastic element is in contact with the plurality of conductive areas on the circuit board.

11. The test strip code reader as claimed in claim 1, wherein the base body further comprises a positioning column, the positioning part further comprises a positioning slot, and the positioning column passes through a positioning through hole of the first conductive element and is inserted in the positioning slot to position the activation element, the first conductive element and the positioning part.

12. The test strip code reader as claimed in claim 1, wherein the base body further comprises a positioning column, and the test strip has a positioning hole for providing a positioning mechanism between the base body and the test strip.

13. The test strip code reader as claimed in claim 1, wherein the base body further comprises a plurality of positioning columns arranged in an asymmetric configuration.

14. The test strip code reader as claimed in claim 13, wherein:
the positioning part further comprises a plurality of first positioning grooves, the first conductive element further comprises a plurality of second positioning grooves and the circuit board further comprises a plurality of positioning through holes;
the plurality of first positioning grooves, the plurality of second positioning grooves and the plurality of positioning through holes are disposed corresponding to the plurality of positioning columns; and
each of the plurality of positioning columns passes through respective ones of the corresponding plurality of first positioning grooves, the corresponding plurality of second positioning grooves and the corresponding plurality of positioning through holes to provide a foolproof assembly mechanism and a positioning reference.

15. An analyte detection system for receiving a test strip to perform an analyte detection, comprising:
a test strip code reader, comprising:
a test strip carrier receiving the test strip;
a first conductive element used as a shared end of a plurality of coding signals;
a plurality of second conductive elements configured to be in a contact state or a separation state with the first conductive element; and
an activation element having a body and a plurality of protrusions, wherein the body and the plurality of protrusions are integrally formed such that the body prevents the first conductive element from being contaminated, and according to whether the plurality of protrusions are actuated by the test strip, the contact state or the separation state between the first conductive element and each of the second conductive elements decodes the code of the test strip;
an upper cover configured above the test strip code reader, and at least partially covering a top surface of the test strip code reader; and
a lower cover configured under the test strip code reader to cover a bottom surface of the test strip code reader.

16. The analyte detection system as claimed in claim 15, wherein the test strip code reader further comprises a circuit board having a conductive area, the conductive area electrically connects to each of the second conductive elements, and a coding signal is responsive to the contact state or the separation state of the first conductive element and the second conductive element.

17. An analyte detection device for detecting a biological sample through a test strip, wherein the test strip has a coding layout, the coding layout has a plurality of coding elements, and the analyte detection device comprises:
a device body;
a plurality of upper operation pieces configured in the device body, and respectively corresponding to the plurality of coding elements;
a plurality of lower operation pieces configured in the device body, and respectively corresponding to the plurality of upper operation pieces, wherein the coding layout is made through a cooperation of the plurality of upper operation pieces and the plurality of lower operation pieces; and
an antipollution element configured in the device body and located between the plurality of upper operation pieces and the plurality of lower operation pieces, and the antipollution elements and the plurality of upper operation pieces are integrally formed to form a one-piece element, wherein the one-piece element has a periphery, and even if the biological sample has an overflow situation in the analyte detection device, the periphery isolates the biological sample from a possible influence on a detection of the biological sample.

* * * * *